(12) United States Patent
Ghyczy

(10) Patent No.: US 6,278,004 B1
(45) Date of Patent: *Aug. 21, 2001

(54) STABILIZED PHOSPHOLIPIDIC COMPOSITION

(75) Inventor: Miklos Ghyczy, Köln (DE)

(73) Assignee: Aventis Pharma Deutschland GmbH, Frankfurt am Main (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/575,404

(22) Filed: May 22, 2000

Related U.S. Application Data

(63) Continuation of application No. 08/955,234, filed on Oct. 21, 1997, now Pat. No. 6,100,413.

(30) Foreign Application Priority Data

Nov. 6, 1996 (DE) .............................................. 196 45 658

(51) Int. Cl.⁷ ....................................................... C11B 5/00
(52) U.S. Cl. ........................ 554/4; 554/2; 554/3; 554/79
(58) Field of Search ................... 554/4, 3, 2, 74

(56) References Cited

U.S. PATENT DOCUMENTS

| | | |
|---|---|---|
| 2,610,973 | 9/1952 | Evans et al. ...................... 260/398.5 |
| 4,192,869 | 3/1980 | Nicolau et al. . |
| 4,321,259 | 3/1982 | Nicolau et al. . |
| 4,397,846 | 8/1983 | Weiner et al. . |
| 4,473,563 | 9/1984 | Nicolau et al. . |
| 4,963,385 | 10/1990 | Antrim et al. ...................... 426/602 |
| 5,059,591 | 10/1991 | Janoff et al. . |
| 5,175,012 | 12/1992 | Shin et al. . |
| 5,446,033 | 8/1995 | Engel et al. . |
| 5,547,676 | 8/1996 | Rocher et al. . |
| 5,552,148 | 9/1996 | Znaiden et al. . |
| 5,683,684 | 11/1997 | Montastier et al. . |
| 5,869,034 | 2/1999 | Montastier et al. . |

FOREIGN PATENT DOCUMENTS

| | | |
|---|---|---|
| 2004409 | 9/1971 | (DE) . |
| 0650720 | 9/1994 | (EP) . |
| 792978 | 4/1958 | (GB) . |
| 47-045401 | 9/1970 | (JP) . |
| 48-007120 | 6/1972 | (JP) . |
| 54-060303 | 5/1979 | (JP) . |
| 59-204696 | 11/1984 | (JP) . |
| 60-153938 | 8/1985 | (JP) . |
| 62-056411 | 12/1987 | (JP) . |
| WO96/17899 | 6/1996 | (WO) . |

OTHER PUBLICATIONS

Derwent Abstract of WO 92/17160.
Derwent Abstract of EP) 595 690.
Derwent Abstract of DE 42 35 911.
Derwent Abstract of DE 28 20 603.
Derwent Abstract of DE 27 40 053.
Derwent Abstract of DE–OS–1 617 542.

*Primary Examiner*—Deborah D. Carr
(74) *Attorney, Agent, or Firm*—Finnegan, Henderson, Farabow, Garrett & Dunner, L.L.P.

(57) ABSTRACT

A method for the stabilization of a phospholipidic composition as well as a method for the production of a stabilized phospholipidic composition comprising at least one phospholipide as well as a stabilizer are described, whereby in the claimed methods at least one phospholipide is mixed with a stabilizer on the basis of phytic acid, of a salt of the phytic acid and/or of a phytic acid derivative.

19 Claims, No Drawings

STABILIZED PHOSPHOLIPIDIC COMPOSITION

RELATED APPLICATION

This application is a continuation of U.S. Ser. No. 08/955,234, filed Oct. 21, 1997, now U.S. Pat. No. 6,100,413.

BACKGROUND OF THE INVENTION

The present invention is directed to a method for the stabilization of a phospholipidic composition, a method for the production of such a composition as well as the use of the stabilized phospholipidic composition.

Phospholipidic compositions have been known for a long time and are used in various ways in the field of food, in food for animals, in the cosmetic field as well as in the pharmaceutical field. Hereby, there is the problem however, that such phospholipidic compositions depending on the concentration of phospholipides and the respective use and being liquid, semisolid, as particularly gel-like, creamy, paste-like, or solid, develop an undesired inherent smell, particularly a rancid inherent smell when exposed to air and/or when stored.

In order to suppress this undesired change of odor of phospholipidic compositions, it is known, to provide the phospholipidic compositions with a stabilizer, whereby such stabilizers are built-up on the basis of vitamin C, vitamin E and/or their derivatives. Furthermore, according to the DE 41 41 842 A1, phospholipidic compositions can also be protected from an undesired oxidation by using N-acyl-phosphatidylethanolamine.

Furthermore the DE 40 21 082 A1 suggests methods which use urea, monosaccharides or mixtures of urea with monosaccharides for the stabilization of phospholipidic compositions.

The object of the present invention is to dispose a method for the stabilization of a phospholipidic composition by which phospholipidic compositions are stabilized in that way that, even when stored for a longer period of time and exposed to air, the odor does not change.

SUMMARY OF THE INVENTION

The inventive method for the stabilization of a phospholipidic composition provides that at least one stabilizer is added to the at least one phospholipide. In the inventive method phytic acid, a salt of the phytic acid and/or a phytic acid derivative, is added as stabilizer to the at least one phospholipidic.

Surprisingly it was observed that the phospholipidic compositions treated according to the inventive method and containing said phytic acid, said salt of the phytic acid and/or said phytic acid derivative as stabilizer, show an excellent stability even when stored under exposure to air, so that an undesired change of odor does not occur with the phospholipidic composition stabilized in such a way, even after a longer period of storage of several months. This leads to the fact that the phospholipidic composition stabilized according to the inventive method does not have to be stored like the other known phospholipidic compositions under inert gas, as for example nitrogen, at reduced temperatures, particularly temperatures around the freezing point. Correspondingly to that, reproducible resultant products regarding the concentration of the phospholipide can be manufactured from the compositions stabilized according to the inventive method, as for example creams, gels, ointments, dispersions, semisolid or liquid liposomal preparations, since the phospholipide concentration remains constant also after a longer storage period.

DETAILED DESCRIPTION OF THE INVENTION

A first embodiment of the composition stabilized according to the inventive method provides a composition that comprises as stabilizer a salt of the phytic acid, particularly an alkaline-earth salt and/or an alkaline salt of the phytic acid.

The phospholipidic composition stabilized according to the inventive method preferably comprises as stabilizer a calcium salt and/or a magnesium salt of the phytic acid, whereby also a mixture of calcium salt and magnesium salt cause a perfect stabilization of the phospholipidic composition.

The afore mentioned phytic acid, the salt of the phytic acid and/or the phytic acid derivative is either a synthetically produced product or a product gained from seed husks and/or from the aleurone layer of grain by the extraction with a watery system and/or with a corresponding solvent. Typical grain sorts from which the phytic acid, the salt of the phytic acid and/or the phytic acid derivative are obtained are wheat, oats, corn, rice, rye, barley and/or millet.

In respect to the derivatives of the phytic acid existing in the composition stabilized according to the inventive method particularly ester, ether, amides, amines and/or their salts are to be mentioned.

With regard to the weight ratio of the at least one phospholipide relative to the phytic acid, to the salt of the phytic acid and/or to the phytic acid derivative in the composition stabilized according to the inventive method, it is to be noted that this weight ratio depends, on one hand, on the desired stabilization and, on the other hand, on the corresponding use of the phospholipidic composition stabilized according to the inventive method.

In the composition stabilized according to the inventive method the weight ratio of the at least one phospholipide to the already described stabilizer normally varies between 1:0.08 to 1:0.002, preferably between 1:0.04 and 1:0.003. If the manufacturing of an extremely long storable phospholipidic composition is desired, then this embodiment comprises a relatively high stabilizer content. The same is the case for such embodiments which are processed as sun protecting products. In other words, by varying the amount of the afore mentioned stabilizers a desired storing stability of the inventive composition can thus be obtained.

With regard to the phospholipide existing in the composition stabilized according to the inventive method, it is to be noted that this is particularly a phospholipide or phospholipide mixture which is isolated from plants, preferably from soy beans.

It is particularly suitable, if the mixture of phospholipides existing in the composition stabilized according to the inventive method comprises at least 70% by weight of 1.2-diacylglycero-3-phosphatidylcholine.

In a further embodiment of the composition stabilized according to the inventive method the mixture of phospholipides existing in the composition comprises at least 76% by weight±3% by weight of 1.2-diacylglycero-3-phosphatidylcholine and 3% by weight±3% by weight of lyso-phosphatidylcholine.

Another, also suitable variation of the embodiment of the composition stabilized according to the inventive method provides that hereby the mixture of phospholipides is a mixture of phospholipides with a high content of phosphatidylcholine, and preferably comprises 93% by weight±3% by weight of 1.2-diacylglycero-3-phosphatidylcholine and particularly at least 96% by weight of 1.2-diacylglycero-3-phosphatidylcholine, whereby as a further phospholipide especially 3% by weight±3% by weight of lyso-phosphatidylcholine additionally exists.

In addition to the phosphatidylcholines already described, the composition stabilized according to the inventive method may also contain preferably 1.2-diacylglycero-3-phosphoethanolamine, 1.2-diacylglycero-3-phosphoinositol, 1.2-diacylglycero-3-phosphoserine, 1.2-diacylglycero-3-phosphoglycerol and 1.2-diacylglycero-3-phosphate as further phospholipides, depending on the respective basic material and the used isolation- and purification method.

A further preferred embodiment of the composition stabilized according to the inventive method comprises such a mixture of phospholipides in which the acyl groups (residues) of the phospholipides existing in the mixture and especially the acyl groups of the phosphatidylcholine provided in the mixture, consist of 61–73% by weight of the linoleic acid residue, 10–14% by weight of the palmitic acid residue, 8–12% by weight of the oleic acid residue, 4–6% by weight of the linolenic acid residue, 3–5% by weight of the stearic acid residue, and/or 2% by weight of other fatty acid residues.

Such a mixture of phospholipides or phosphatidylcholines or the mixtures described more precisely in the following, particularly show the advantages described above for the composition stabilized according to the inventive method, since such phospholipides, respectively such phosphatidylcholines, very quickly tend to generate an inherent smell growing in intensity when being stored even under exclusion from atmospheric oxygen, because of their high concentration of unsaturated fatty acid residues even with a high purity factor.

A further embodiment of the composition stabilized according to the inventive method provides a composition which comprises a mixture of phospholipides or a phosphatidylcholine in which the 1-acyl groups (residues) of the phospholipides existing in the mixture, respectively the 1-acyl groups of the phosphatidylcholine, consist of 45–61% by weight of the linoleic acid residue, 19–26% by weight of the palmitic acid residue, 8–12% by weight of the oleic acid residue, 4–6% by weight of the linolenic acid residue, 6–9% by weight of the stearic acid residue, and/or 2% by weight of other fatty acid residues.

The composition stabilized according to the inventive method can also comprise such a mixture of phospholipides or phosphatidylcholine, the acyl groups of which comprise in the 1-position the already described acyl groups or other acyl groups. The acyl groups in the 2-position of such a mixture of phospholipides or phosphatidylcholine consist of 77–85% by weight of the linoleic acid residue, 1–2% by weight of the palmitic acid residue, 8–12% by weight of the oleic acid residue, 4–6% by weight of the linolenic acid residue, 0–1% by weight of the stearic acid residue, and/or 2% by weight of other fatty acid residues.

A further embodiment of the composition stabilized according to the inventive method provides a composition which comprises as a mixture of phospholipides a liquid mixture of phospholipides being isolated from plants, preferably from soy beans, whereby this liquid mixture of phospholipides contains at least 40% by weight of 1.2-diacylglycero-3-phosphatidycholine. Furthermore this liquid mixture of phospholipides contains the usual accompanying phospholipides as well as oils, preferably vegetable oils, as particularly sunflower oil, thistle oil, avocado oil, almond oil, soy oil, castor oil, peanut oil, wheat germ oil, carrot oil, hazelnut oil, palm kernel oil, sesame oil, olive oil, walnut oil, corn oil and others.

As a further essential advantage of the afore described composition stabilized according to the inventive method it is to be noted that by, adding the above mentioned stabilizers to the phospholipidic composition, also the resultant products generated from the phospholipidic composition stabilized according to the inventive method, as particularly the afore indicated creams, gels, ointments, dispersion, semi-solid of liquid liposomal preparations are stabilized, so that the addition of a separate stabilizer to these resultant products is not necessary.

The present invention is furthermore directed to a method for the production of the above described stabilized phospholipidic composition.

This object is realized according to the invention by the claimed method of production.

The inventive method for the production of the afore described stabilized phospholipidic composition provides that the at least one phospholipide or the mixture of phospholipides is firstly dissolved or dispersed in a solvent or mixture of solvents. Hereafter, this solution or this dispersion of the phospholipide or the mixture of phospholipides is added to a solution or dispersion of the stabilizer already described, in such a way that the mixture produced in such a way by formation of the stabilized phospholipidic composition is then carefully dried, especially spray-dried or freeze-dried.

The inventive method provides the advantage that it can be performed in a relatively easy manner. This is based on the fact, that with the inventive method only two solutions or dispersions are mixed together, so that hereafter only this mixture is dried and that thus the inventive stabilized composition emerges. It is also possible, of course, with the already described inventive method, to add the solution or dispersion of the stabilizer to the solution or dispersion of the phospholipide or mixture of phospholipides and, hereafter to carefully dry, especially spray-dry or freeze-dry this mixture.

In respect to the selection of the solvent, respectively the mixture of solvents used in the inventive method it is basically to be stated, that the solvent, respectively the mixture of solvents for the phospholipide, respectively the mixture of phospholipides, and the solvent, respectively the mixture of solvents, for the stabilizer are correspondingly adjusted to each other in such a way, that these two solvents, respectively mixtures of solvents, are mixable between each other. As a solvent or as a mixture of solvents for the inventive method, preferably water and/or an alcohol, respectively a mixture of alcohols, particularly ethanol, propanol-1 and/or propanol-2, are used.

A particularly suitable and advantageous embodiment of the inventive method provides, that hereby an alcoholic solution of the phospholipide or the mixture of phospholipides is produced, especially an ethanolic solution of the phospholipide or mixture of phospholipides, and that thereafter this alcoholic solution is stirred or injected into an aqueous dispersion or an aqueous solution of the stabilizer.

In the present description by water all those kinds of water systems are meant, as particularly distilled water, deionized water, aqueous salt solutions or aqueous buffer systems, as for example phosphate buffers.

With regard to the concentration of the phospholipide or the mixture of phospholipides in the alcoholic solution, it is to be noted that in the inventive method usually this alcoholic solution comprises between 70% by weight and 85% by weight of the phospholipide or of the mixture of phospholipides. Correspondingly, this alcoholic solution of phospholipides then comprises between 30% by weight and 15% by weight of the alcohol, especially ethanol.

Another embodiment of the inventive method provides that hereby an aqueous dispersion of the phospholipide is produced and that this aqueous dispersion of the phospholipide is then stirred or injected into the aqueous dispersion of the stabilizer. This variation of the inventive method provides the advantage, that it can be renounced on alcohol as a solvent, so that this variation of the inventive method is preferred in those cases, where the respective manufacturer does not dispose of the corresponding equipment which allows the processing of inflammable solvents.

The aqueous dispersion already described preferably comprises between 5% by weight and 20% by weight, particularly between 8% by weight and 15% by weight, of the phospholipide or mixture of phospholipides.

If in the inventive method an aqueous dispersion or an aqueous solution of the afore mentioned stabilizers is used, it is advisable that hereby the aqueous dispersion, respectively solution, of the stabilizer contains between 10% by weight and 30% by weight, particularly between 15% by weight and 20% by weight, of the stabilizer. By adjusting the amount of this solution, respectively dispersion, relative to the amount of the phospholipide solution, respectively the phospholipide dispersion, a weight ratio of phospholipide, respectively mixture of phospholipides, to the stabilizer of 1:0.08 to 1:0.002, preferably between 1:0.04 and 1:0.003, can be adjusted in a relatively simple manner for the manufacturing of the inventive composition.

If, by the already described variations of the inventive method, further substances shall be added, as for example the afore mentioned oils, so that accordingly the stabilized composition produced in such a way comprises these further substances, then this can be achieved basically in three different ways.

The first possibility provides that hereby these further substances are added to the solution, respectively to the dispersion of the phospholipide, whereas the second possibility provides that these further substances are added to the solution, respectively to the dispersion of the stabilizer. As a third possibility also a separate solution, respectively dispersion, of these further substances can be produced, whereby this solution, respectively dispersion, is then added to the mixture of the solution of the phospholipides, respectively the dispersion of the phospholipides, and to the solution of the stabilizer, respectively to the dispersion of the stabilizer.

A further possibility for the production of the stabilized composition provides that hereby a liquid phospholipide, respectively a liquid mixture of phospholipides, is produced in such a way, that the phospholipide, respectively the mixture of phospholipide, is added to an oil, particularly to the already described oils or to the mixtures of oils. Hereafter the phospholipide, respectively the mixture of phospholipides, added to the oil is mixed with the dispersion, respectively the solution, of the stabilizer under the formation of the stabilized composition.

It is certainly possible to liquefy the phospholipide or mixture of phospholipides in a variation of the already described method in such a way, that it is not added to an oil but instead of that the phospholipide or mixture of phospholipides itself is molten by the use of higher temperatures, and the phospholipide, respectively the mixture of phospholipides, molten in such a way, is then mixed with the solid stabilizer or with a solution, respectively a dispersion, of the stabilizer.

With regard to the use of the inventive composition, it is to be stated that the inventive composition is used especially for the production of cosmetics or pharmaceutical products. In respect to the cosmetics, the stabilized composition can be used preferably for the production of skin care products, particularly the usual ointments, creams, lotions, milks, basic components for ointments and/or basic components for creams.

In the pharmaceutical field, the main field of use of the inventive composition especially exists in the production of semisolid, gel-like of solid basic substances, as for example of corresponding lotions, creams, gels, ointments which are topically applied after the adding of suitable active ingredients. From the composition stabilized according to the invention also liquid formulations can be generated, whereby such liquid formulations additionally comprise one or several active ingredients.

Advantageous developments of the inventive method are indicated in the subclaims.

The inventive method is explained in detail in the following by means of examples.

EXAMPLE 1

800 g of a phospholipide, which comprises at least 96% by weight of phosphatidylcholine as well as other accompanying phospholipides, were dissolved in 200 g of alcohol. The solution prepared in such a way was titled solution 1.

4 g of phytic acid were solved in 800 g of water. The solution prepared in such a way was titled solution 2.

100 g of the solution 1 were mixed with 200 g of the solution 2, whereby the mixing process occurred by means of a fast running stirring device (1.000 rpm) for a period of 5 minutes. Thereafter the liquid mixture prepared in such a way was subjected to the usual spray-drying.

Hereby a phospholipidic composition I was produced having a weight ratio of phospholipide to stabilizer of 1:0.0025.

EXAMPLE 2

50 g of the solution 1 were mixed with 200 g of the solution 2, each prepared according to example 1 under the conditions mentioned therein.

The composition prepared in such a way had a weight ratio of phospholipide to stabilizer of 1:0.005 after spray-drying.

EXAMPLE 3

50 g of the solution 1 were mixed with 400 g of the solution 2, prepared according to example 1 under the conditions mentioned therein. After the spray-drying the composition III prepared in such a way had a weight ratio of phospholipide to stabilizer of 1:0.01.

EXAMPLE 4

50 g of the solution 1 were mixed with 800 g of the solution 2, prepared according to the conditions mentioned in example 1. After the spray-drying the composition IV had a mixture ratio of phospholipide to stabilizer of 1:0.02.

EXAMPLE 5

100 g of the solution 1 were mixed with 200 g of the solution 2, prepared according to the conditions mentioned in example 1. 3 g of a sunflower oil were dripped into the mixture while stirring, whereby the so produced dispersion/emulsion was stirred for further 10 minutes. The mixture prepared in such a way was spray-dried. Thereafter a composition was generated which in the following is titled composition V and which had a weight ratio of phospholipide to stabilizer of 1:0.0025.

EXAMPLE 6

80 g of the phospholipide described in example 1 were solved in 20 g of ethanol. 2 g of tocopherole were stirred into this alcoholic solution. Thereafter it was spray-dried. The so prepared composition VI had weight ratio of phospholipide to stabilizer of 1:0.025.

An aging test was performed with the already mentioned compositions I to VI to that effect that the inherent smell of the compositions was judged by four people independent from each other, directly after the production as well as after a storage period of one week, of one month, of three months and of six months. For reasons of objectivity a freshly prepared sample of the corresponding composition was also judged in comparison in this sensory rating of the odor. The formation of the odor was rated according to a random classification entailing the marks 1 to 4, whereby the mark 1 represents no change of odor and the mark 4 represents a strong rancid impression of odor. The mark 2 rates a low change of odor, the mark 3 a correspondingly stronger change of odor.

The results of this sensory rating of odor are described in the following table.

TABLE 1

| composition No. | directly after the production | after one week | after one month | after three months | after six months |
|---|---|---|---|---|---|
| I | 1 | 1 | 1 | 2 | 2 |
| II | 1 | 1 | 1 | 1 | 1 |
| III | 1 | 1 | 1 | 1 | 1 |
| IV | 1 | 1 | 1 | 1 | 1 |
| V | 1 | 1 | 1 | 1 | 1 |
| VI | 1 | 1 | 2 | 3 | 3 |

What is claimed is:

1. A phospholipidic composition comprising at least one phospholipid as well as a stabilizer, whereby said stabilizer is selected from the group consisting of phytic acid, a salt of the phytic acid, a phytic acid derivative and mixtures thereof.

2. The composition according to claim 1 wherein said composition comprises as stabilizer a salt of the phytic acid.

3. The composition according to claim 2, wherein said salt of the phytic acid is an alkaline-earth salt, an alkaline salt of the phytic acid or a mixture thereof.

4. The composition according to claim 3, wherein said alkaline-earth salt is a calcium salt of the phytic acid, a magnesium salt of the phytic acid or mixtures thereof.

5. The composition according to claim 1, wherein the weight ratio of said at least one phospholipid to said stabilizer varies between 1:0.08 to 1:0.002.

6. The composition according to claim 1, wherein the weight ratio of said at least one phospholipid to said stabilizer varies between 1:0.04 and 1:0.003.

7. The composition according to claim 1, wherein said phospholipid is isolated from plants.

8. The composition according to claim 7, wherein said phospholipid is isolated from soy beans.

9. The composition according to claim 1, wherein said at least one phospholipid is a mixture of phospholipids.

10. The composition according to claim 9, wherein said mixture of phospholipids contains at least 70% by weight of 1,2-diacylglycero-3-phosphatidylcholine.

11. The composition according to claim 10, wherein said mixture of phospholipids comprises at least:
   76% by weight±3% by weight of 1,2-diacylglycero-3-phosphatidylcholine, and
   3% by weight±3% by weight of lyso-phosphatidylcholine.

12. The composition according to claim 10, wherein said mixture of phopholipids comprises at least:
   93% by weight±3% by weight of 1,2-diacylglycero-3-phosphatidylcholine, and
   3% by weight±3% by weight of lyso-phosphatidylcholine.

13. The composition according to claim 9, wherein said mixture of phospholipids further comprises 1,2-diacylglycero-3-phosphoethanolamine, 1,2-diacylglycero-3-phosphoinositol, 1,2 -diacylglycero-3-phosphoserine, 1,2-diacylglycero-3-phosphoglycerol,and/or 1,2-diacylglycero-3-phosphate.

14. The composition according to claim 1, wherein said at least one phospholipid comprises such a mixture of phospholipids in which acyl groups of the phospholipids existing in the mixture consist of:
   61–73% by weight of linoleic acid residue,
   10–14% by weight of palmitic acid residue,
   8–12% by weight of oleic acid residue,
   4–6% by weight of linolenic acid residue,
   3–5% by weight of stearic acid residue, and/or
   2% by weight of other fatty acid residues.

15. The composition according to claim 1, wherein said at least one phospholipid comprises such a mixture of phospholipids in which 1-acyl groups of the phospholipids existing in the mixture consist of:
   45–61% by weight of linoleic acid residue,
   19–26% by weight of palmitic acid residue,
   8–12% by weight of oleic acid residue,
   4–6% by weight of linolenic acid residue,
   6–9% by weight of stearic acid residue, and/or
   2% by weight of other fatty acid residues.

16. The composition according to claim 1, wherein said at least one phospholipid comprises such a mixture of phospholipids in which 2-acyl groups of the phospholipids existing in the mixture consist of:
   77–85% by weight of linoleic acid residue,
   1–2% by weight of palmitic acid residue,
   8–12% by weight of oleic acid residue,
   4–6% by weight of linolenic acid residue,
   0–1% by weight of stearic acid residue, and/or
   2% by weight of other fatty acid residues.

17. The composition according to claim 1, wherein said at least one phospholipid comprises a liquid mixture of phospholipids being isolated from soy beans and which contains at least 40% by weight of 1,2-diacylglycero-3-phosphatidylcholine as well as the usual accompanying phospholipids and oils.

18. The composition according to claim 17, wherein said oil is a vegetable oil.

19. The composition according to claim 18, wherein said vegetable oil is selected from the group consisting of sunflower oil, thistle oil, avocado oil, almond oil, soy oil, castor oil, peanut oil, wheat germ oil, carrot oil, hazelnut oil, palm kernel oil, sesame oil, olive oil, walnut oil, corn oil and mixtures thereof.

* * * * *